United States Patent [19]

Stockel

[11] Patent Number: 4,921,691
[45] Date of Patent: May 1, 1990

[54] SPRAY ON WOUND DRESSING COMPOSITIONS

[76] Inventor: Richard F. Stockel, 475 Rolling Hills Rd., Bridgewater, N.J. 08807

[21] Appl. No.: 768,422

[22] Filed: Aug. 22, 1985

[51] Int. Cl.$^5$ ............................................. A61L 9/04
[52] U.S. Cl. .................................................. 424/45
[58] Field of Search ...................................... 424/45

[56] References Cited

U.S. PATENT DOCUMENTS

| | | | |
|---|---|---|---|
| 2,265,450 | 12/1941 | Reppe et al. | 260/239.3 R |
| 2,801,201 | 7/1957 | Kipnis | 424/115 |
| 2,804,073 | 8/1957 | Gallienne et al. | 424/81 |
| 2,972,545 | 2/1961 | Briskin | 514/781 |
| 3,073,794 | 1/1963 | Stoner | 424/59 |
| 3,079,299 | 2/1963 | Heilig | 424/83 |
| 3,269,903 | 8/1966 | Von Fieandt et al. | 424/45 |
| 3,471,541 | 10/1969 | Morehouse | 556/422 |
| 3,476,853 | 11/1969 | Jatul et al. | 424/45 |
| 3,560,385 | 2/1971 | Roth | 252/49.6 |
| 3,572,330 | 3/1971 | Gander | 424/45 |
| 3,577,516 | 5/1971 | Gould et al. | 424/46 |
| 3,730,701 | 5/1973 | Isquith et al. | 71/67 |
| 3,817,739 | 6/1974 | Abbott et al. | 71/67 |
| 3,865,728 | 2/1975 | Abbott et al. | 71/67 |
| 3,928,556 | 12/1975 | Sweger | 424/45 |
| 3,932,602 | 1/1976 | Sweger | 424/45 |
| 4,005,028 | 1/1977 | Heckert et al. | 546/428 |
| 4,005,030 | 1/1977 | Heckert et al. | 556/422 |
| 4,394,378 | 7/1983 | Klein | 514/63 |

FOREIGN PATENT DOCUMENTS

| | | | |
|---|---|---|---|
| 1589917 | 5/1970 | France | 424/45 |
| 814001 | 5/1959 | United Kingdom | 424/45 |
| 1433303 | 4/1976 | United Kingdom . | |

*Primary Examiner*—Douglas W. Robinson
*Attorney, Agent, or Firm*—Walter Katz

[57] ABSTRACT

A spray on wound dressing composition comprises an anti-microbial, film-forming compound which is an anti-bacterial organosilicon quaternary ammonium salt chemically bonded to a film-forming organic polymer, and a propellant solvent.

16 Claims, No Drawings

SPRAY ON WOUND DRESSING COMPOSITIONS

BACKGROUND OF THE INVENTION

1. Field of the Invention

This invention relates to spray on wound dressing bandages, and, more particularly, to compositions suitable for forming an anti-microbial film dressing including a permanently bound, effective anti-microbial agent.

2. Description of the Prior Art

The advantages of using a spray on wound dressing in place of gauze bandages for protection of wounds from infection and water is described in U.S. Pat. No. 2,801,201; 2,804,073; 2,972,545; 3,073,794; 3,079,299; 3,269,903; 3,476,853; 3,577,516; and 3,932,602; and in the J. Biomedical Material Research, Vol. 6, p. 571-590 (1972). Generally such wound dressings are compositions of two components, namely, a film-forming polymer and an anti-microbial substance, which are applied as a liquid, or sprayed with an aerosol propellant.

The requirements of a suitable spray on wound dressing is an ability to form a flexible non-irritating thin polymer film which is innocuous to the wound, which conforms to the skin surface and exhibits good skin adhesion, possesses a high moisture transmission rate to permit some wound excretion to pass through the film and evaporate moisture from the covered surface, and which prevents bacterial and dirt invasion. These and other attributes of an idealized spray on wound dressing, while known, have been difficult to achieve in prior art compositions for this use.

Accordingly, it is an object of the present invention to provide an improved spray on wound dressing composition.

Another object herein is to provide a spray on wound dressing capable of forming an anti-microbial film which is non-toxic, non-irritating, flexible, skin conformal and air permeable and which allows the epitheral tissue to regrow without substantial water loss.

A specific object of this invention is to provide an improved spray on wound dressing composition in which both the anti-microbial and film-forming components of the composition are present in one compound.

These and other objects and features of the invention will be made apparent from the following particular description of the invention.

SUMMARY OF THE INVENTION

What is described herein is an improved spray on wound dressing composition which comprises a compound which is an anti-microbial organosilicon quaternary ammonium salt chemically bonded to a film-forming organic polymer, and a suitable propellant solvent therewith.

The organosilicon quaternary ammonium salt constitutes 2 to 30 wt. % by weight of the compound, and the organic polymer is 70-98% by weight of the compound. The composition itself comprises 2-30 wt. % by weight of the anti-microbial film-forming compound, the rest being a propellant solvent.

In the preferred forms of the invention, the organosilicon quaternary ammonium salts are 3-(trimethoxysilyl) propyloctadecyldimethyl ammonium chloride, bromide or triiodide, 3-(dimethoxymethylsilyl) propyloctadecyldimethyl ammonium chloride, bromide or triiodide, or 3-(methoxydimethylsilyl) propyloctadecyldimethyl ammonium chloride, bromide or triiodide, and the organic polymer is polyvinylpyrrolidone, in a propellant solvent, preferably a chlorofluorohydrocarbon or a high vapor pressure, low boiling solvent, such as methanol, ethanol, acetone, ethyl acetate, methylene chloride, and the like, and mixtures thereof.

DETAILED DESCRIPTION OF THE INVENTION

The organic polymers used in the compound and compositions of this invention include such polymers as polyvinylpyrrolidone, e.g. PVP-K30 polymer, and those related polymers disclosed in U.S. Pat. No. 3,073,794; cellulosic polymers, e.g. ethyl hydroxyethyl cellulose, e.g. Klucel ® (Hercules); polyhydroxy and alkoxy alkyl acrylates and methacrylates, e.g. polyhydroxypropyl acrylates, ethoxyethyl acrylates and the corresponding methacrylates; polyacrylamides and derivatives thereof; polysaccharides; protein-type polymers such as gelatin and collagin; and mixtures thereof.

The anti-microbial organosilicon quaternary ammonium salt compounds and their preparation are described in the literature, as for example, in U.S. Pat. Nos. 3,471,541; 3,560,385; 3,730,701; 3,817,739; 3,865,728; 4,005,028; 4,005,030; 4,394,378 and British Pat. No. 1,433,303. Particularly useful are those compounds described in U.S. Pat. Nos. 3,730,701, 3,817,739 and 4,394,378.

The essential characteristics of such compounds are anti-microbial activity, usually imparted by the presence of a long chain alkyl group on the quaternary nitrogen atom and a hydrolyzable group on the silicon atom which can be reacted with polymer. Generally the hydrolyzable group is a hydrolyzable hydrocarbonoxy group such as alkoxy or acyloxy, for reaction with an active hydrogen of the polymer. In water solution, alkoxy and acyloxy groups are hydrolyzed to hydroxyl groups, i.e., a silanol, for reaction with the polymer.

A useful class of anti-microbial organosilicon quaternary ammonium salts are described in U.S. Pat. No. 3,730,701 and has the general formula:

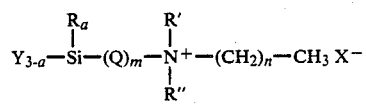

where
Y is a hydrolyzable radical, e.g. a hydrocarbonoxy group; e.g. alkoxy, or acyloxy;
R is a monovalent hydrocarbon group, e.g. lower alkyl or phenyl;
a is 0-2;
Q is a divalent hydrocarbon radical, e.g. alkylene or phenylene;
m is 1-20;
R' is alkyl $C_1$-$C_{18}$, aryl, alkaryl, or aralkyl;
R" is lower alkyl;
n is 9-17;
X is monovalent inorganic or organic radical or group selected from halogen; triiodide; acyloxy; or $YSO_4$,
where Y is a monovalent hydrocarbon, hydrogen, or —$(CH_2$—$)_x$—COOR''', where x is at least 2 and R''' is a monovalent hydrocarbon group free of unsaturation.
Particularly useful compounds are those in which:
Y is alkoxy; e.g. methoxy;
R is lower alkyl; e.g. methyl;
m is 2-4; e.g. 3;

R' is lower alkyl or aralkyl; e.g. methyl or benzyl;
R" is lower alkyl;
n is 11–17, and
X is halogen or triiodide.

Some representative compounds are the following:
Typical organosilicon quaternary ammonium salts compounds for use herein include the following:

(1) 3-(trimethoxysilyl)propyloctadecyldimethyl ammonium chloride

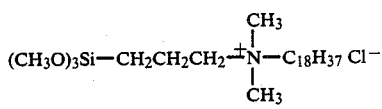

(2) 3-(triethoxysilyl)propyloctadecyldimethyl ammonium chloride

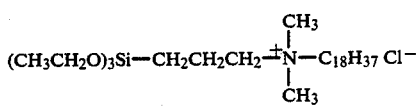

(3) 3-(methyldimethoxysilyl)propyloctadecyldimethyl ammonium chloride

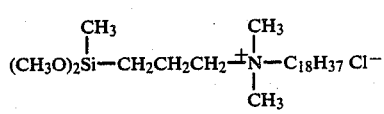

(4) 3-(phenyldimethoxysilyl)propyloctadecyldimethyl ammonium chloride

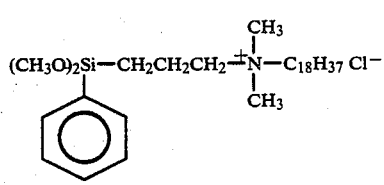

(5) 3-(dimethylmethoxysilyl)propyloctadecyldimethyl ammonium chloride

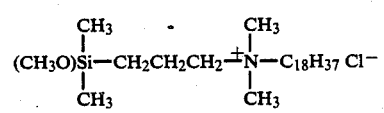

(6) 3-(diphenylmethoxysilyl)propyloctadecyldimethyl ammonium chloride

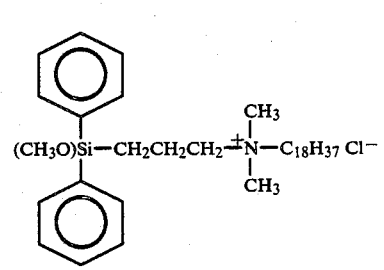

(7) 6-(methyldimethoxy)hexyloctadecyldimethyl ammonium chloride

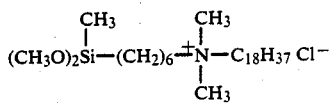

(8) 8-(methyldimethoxysilyl)octyloctadecyldimethyl ammonium chloride

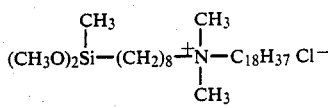

(9) 12-(methyldimethoxysilyl)dodecyloctadecyldimethyl ammonium chloride

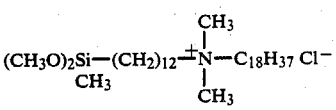

(10) 3-(methyldimethoxysilyl)propylmethyldidodecyl ammonium chloride

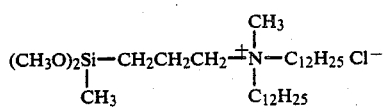

(11) 3-(methyldimethoxysilyl)propylmethyldodecylbenzyl ammonium chloride

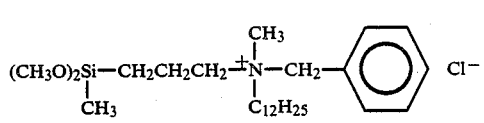

(12) 3-(methyldimethoxysilyl)propylbenzyldidodecyl ammonium chloride

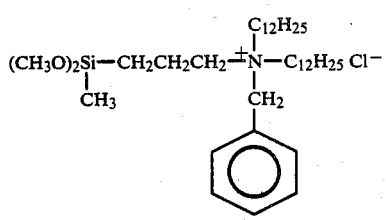

(13) 3-(trimethoxysilyl)propyloctadecyldimethyl ammonium bromide

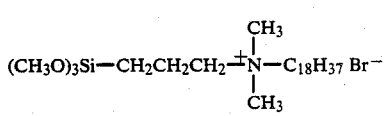

(14) 3-(trimethoxysilyl)propyloctadecyldimethyl ammonium triiodide

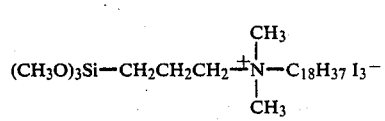

(15) 3-(trimethoxysilyl)propyloctadecyldimethyl ammonium acetate

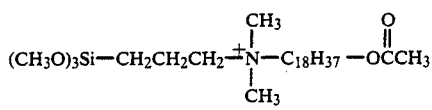

(16) 3-(trimethoxysilyl)propyloctadecyldimethyl ammonium sulfate

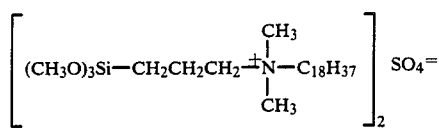

(17) 3-(methoxydimethylsilyl)propylomethyldidodecyl ammonium triiodide

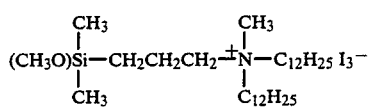

(18) 2-(trimethoxysilyl)ethyl p-benzyl dimethyloctadecyl ammonium chloride

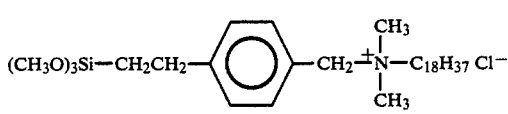

(19) 2-(trimethoxysilyl)ethyl-4-methylcyclohexyl dimethyl octadecyl ammonium chloride

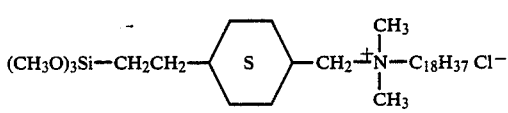

The reaction between organosilicon quaternary ammonium halide and polymer is carried out in water solution, or in water-alcohol mixtures, suitably with about 2-30 wt. of said organosilicon halide, and about 70 to 98 wt % of the polymer. The reaction medium can be acidic, neutral or alkaline.

The water soluble polymers used herein are of a sufficiently, high molecular weight, so that they cannot readily be adsorbed through the skin.

The preparation of polyvinylpyrrolidone (PVP) is well documented in the literature; see U.S. Pat. No. 2,265,450. It can be obtained in various degrees of polymerization designated by Fichentscher K value. A preferred grade used in formulations is the pharmaceutical grade with an average molecular weight of about 40,000 and is available from GAF Corporation. Water-soluble PVP having average molecular weights of from several thousand to several hundred thousand are within the scope and spirit of the invention, e.g., from about 10,000 to about 250,000, and higher; however, commercially available PVP are, for obvious economic reasons, most suitable.

EXAMPLE 1

A spray on wound dressing composition is prepared by mixing the compound 3-(trimethoxysilyl) propyl octadecyldimethyl ammonium chloride chemically bound to polyvinylpyrrolidone (PVP-K30) polymer, in the ratio of 15% by weight of the silane quat to 85% by weight of the polymer, with Freon 21 (dichlorofluoromethane) propellant in the ratio of 10% by weight of the compound to 90% by weight of the propellant. The spray on composition then is applied to an abraded skin surface to provide an anti-microbial film dressing thereon. The dressing is able to conform to the surface of the skin, is flexible, non-toxic, non-tacky and non-irritating, dries rapidly, inhibits water loss from the skin surface while permitting air free of bacteria and dirt from entering the wound.

EXAMPLE 2

A spray on wound dressing composition is prepared from (a) 10% by weight of the reaction product of 8% by weight of 3-(triethoxysilyl) propyloctadecyldimethyl ammonium chloride and 92% by weight of PVP-K30 (GAF Corp.) and (b) 90% by weight of Freon 21 (dichlorofluoromethane) in a pressure vessel equipped with a spray nozzle. The aerosol spray composition is stable over a wide temperature range and upon application to a skin wound gives a suitable dressing.

EXAMPLE 3

A spray on wound dressing composition is prepared from (a) 15% by weight of the polymer reaction product of 5% by weight of 3-(dimethoxymethylsilyl) propyloctadecyldimethyl ammonium chloride and 95% by weight of ethyl hydroxyethyl cellulose and (b) 60% by weight of Freon 21, 5% by weight of ethyl acetate and 20% methanol, in a pressure vessel equipped with a spray nozzle. The aerosol spray composition is stable over a wide temperature range and upon application to a skin wound gives a suitable dressing.

EXAMPLE 4

A spray on wound dressing composition is prepared from (a) 20% by weight of the reaction product of 10% by weight of 3-(trimethoxysilyl) propyl dioctadecylmethyl ammonium chloride and 90% by weight of poly hydroxyethyl acrylate, and (b) 55% by weight of Freon 21, 5% by weight of ethyl acetate and 20% by weight methanol, in a pressure vessel equipped with a spray nozzle. The aerosol spray composition is stable over a wide temperature range and upon application to a skin wound gives a suitable dressing.

While the invention has been described with particular reference to certain embodiments thereof it will be understood that changes and modifications may be made which are within the skill of the art. It is intended to be bound only by the appended claims in which what is claimed is:

1. A spray on wound dressing composition comprising
   (a) 2-30% by weight of an anti-bacterial, film-forming compound which is the reaction product of
      (i) 2 to 30% by weight of an organo-silicon quaternary ammonium salt which includes a hydrolyzable silane group, and
      (ii) 70 to 98% by weight of an organic polymer reactive with said hydrolyzable group, and
   (b) the rest being a propellant solvent.

2. A spray on wound dressing composition according to claim 1, wherein said organosilicon quaternary ammonium salt is 3-(trimethoxysilyl) propyloctadecyldimethyl ammonium chloride, bromide or triiodide.

3. A spray on wound composition according to claim 1, wherein said organosilicon quaternary ammonium salt is 3-(dimethoxymethylsilyl) propyloctadecyldimethyl ammonium chloride, bromide or triiodide.

4. A spray on wound dressing composition according to claim 1, wherein said organosilicon quaternary ammonium salt is 3-(methoxydimethylsilyl) propyloctadecyldimethyl ammonium chloride, bromide or triiodide.

5. A spray on wound dressing composition according to claim 1, wherein said polymer is a polyvinylpyrrolidone, cellulosic polymer, poly hydroxy and alkoxyalakyl acrylate or methacrylate, polyacrylamide, or polysaccharide, or mixtures thereof.

6. A spray on wound dressing composition according to claim 1, wherein said polymer is polyvinylpyrrolidone.

7. A spray on wound dressing composition according to claim 1, wherein said propellant solvent is a chlorofluorohydrocarbon, methanol, ethanol, ethyl acetate, methylene chloride, and mixtures thereof.

8. A spray on wound dressing composition according to claim 1, wherein said propellant solvent is a chlorofluorohydrocarbon.

9. A spray on wound dressing composition according to claim 1, wherein said polymer is polyvinylpyrrolidone and said propellant solvent is a dichlorofluoromethane.

10. A spray on wound dressing composition according to claim 1, wherein said compositions comprises (a) 10% by weight of the reaction product of 15% by weight of 3-(trimethoxysilyl) propyloctadecyldimethyl ammonium chloride and 85% by weight of polyvinylpyrrolidone, and (b) 90% by weight of dichloro fluoromethane.

11. A spray on wound dressing composition according to claim 1, wherein said composition comprises (a) 10% by weight of the reaction product of 8% by weight of 3-(triethoxysilyl) propyloctadecyldimethyl ammonium chloride and 92% by weight of polyvinylpyrrolidone, and (b) 90% by weight of dichlorofluoromethane.

12. A spray on wound dressing composition according to claim 1, wherein said composition comprises (a) 15% by weight of the reaction product of 5% by weight of 3-(dimethoxymethylsilyl) propyloctadecyldimethyl ammonium chloride and 95% by weight of ethyl hydroxyethyl cellulose, and (b) 60% by weight of Freon 21, 5% by weight of ethyl acetate and 20% by weight of methanol.

13. A spray on wound dressing composition according to claim 1, wherein said composition comprises (a) 20% by weight of the reaction product of 10% by weight of 3-(trimethoxysilyl) propyldioctadecyl methyl ammonium chloride and 90% by weight of polyhydroxyalkyl acrylate and (b) 55% by weight of dichlorofluoromethane, 5% by weight of athyl acetate and 20% by weight of methanol.

14. A spray on wound dressing composition according to claim 1, wherein said composition comprises (a) 20% by weight of the reaction product of 10% by weight of 3-(dimethylmethoxysilyl) propyloctadecyldimethyl ammonium chloride and 90% by weight of polyvinylpyrrolidone and (b) 55% by weight of dichlorofluoromethane, 5% by weight of ethyl acetate and 20% by weight of methanol.

15. The film product made by applying the composition of claim 1 to the skin.

16. A spray on wound dressing composition according to claim 1 wherein said organosilicon quaternary ammonium salt has the formula:

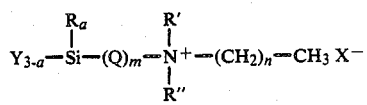

where
Y is a hydrolyzable radical, selected from a hydrocarbonoxy group; selected from alkoxy, or acyloxy;
R is a monovalent hydrocarbon group, selected from lower alkyl or phenyl;
a is 0-2;
Q is a divalent hydrocarbon radical, selected from alkylene or phenylene;
m is 1-20;
R' is alkyl $C_1$-$C_{18}$, aryl, alkaryl, or aralkyl;
R" is lower alkyl;
n is 9-17;
X is monovalent inorganic or organic radical or group selected from halogen; triiodide; acyloxy; or $YSO_4$, where Y is a monovalent hydrocarbon, hydrogen, or —$(CH_2—)_x$—COOR''', where x is at least 2 and R''' is a monovalent hydrocarbon group free of unsaturation.

* * * * *